US012304894B2

(12) United States Patent
Fardella Bello et al.

(10) Patent No.: US 12,304,894 B2
(45) Date of Patent: May 20, 2025

(54) DERIVATIVES OF ADAMANTYL OXADIAZOLES AND PHARMACEUTICALLY ACCEPTABLE SOLVATES, HYDRATES AND SALTS THEREOF, PHARMACEUTICAL COMPOSITION COMPRISING SAME, SYNTHESIS METHOD, SUITABLE FOR USE AS EFFECTIVE AND SELECTIVE INHIBITORS OF THE REDUCTASE ACTIVITY OF THE ENZYME 11-BETA DEHYDROGENASE TYPE 1 (11β-HSD1)

(71) Applicant: PONTIFICIA UNIVERSIDAD CATOLICA DE CHILE, Santiago (CL)

(72) Inventors: Carlos Enrique Fardella Bello, Santiago (CL); Carlos Fernando Lagos Arévalo, Santiago (CL); Andrea Paola Vecchiola Cárdenas, Santiago (CL); Fidel Alejandro Allende Sanzana, Santiago (CL); Benjamin Manuel Diethelm Varela, Santiago (CL); Gonzalo Ivan Recabarren Gajardo, Santiago (CL); Pablo Marcelo González Cisterna, Santiago (CL)

(73) Assignee: PONTIFICIA UNIVERSIDAD CATOLICA DE CHILE, Santiago (CL)

( * ) Notice: Subject to any disclaimer, the term of this patent is extended or adjusted under 35 U.S.C. 154(b) by 804 days.

(21) Appl. No.: 17/604,194

(22) PCT Filed: Apr. 17, 2019

(86) PCT No.: PCT/CL2019/050029
§ 371 (c)(1),
(2) Date: Oct. 15, 2021

(87) PCT Pub. No.: WO2020/210922
PCT Pub. Date: Oct. 22, 2020

(65) Prior Publication Data
US 2022/0194909 A1 Jun. 23, 2022

(51) Int. Cl.
*C07D 271/06* (2006.01)
*C07D 413/10* (2006.01)

(52) U.S. Cl.
CPC ......... *C07D 271/06* (2013.01); *C07D 413/10* (2013.01)

(58) Field of Classification Search
CPC .. C07D 413/06; C07D 273/02; C07D 413/10; C07D 271/06; A61K 31/4245; A61K 31/4439
USPC ................ 546/269.1; 548/131; 514/340, 364
See application file for complete search history.

(56) References Cited

U.S. PATENT DOCUMENTS

2009/0264650 A1    10/2009   Cho et al.

FOREIGN PATENT DOCUMENTS

| CL | 201500130 | 6/2015 |
| WO | 03065983 A2 | 8/2003 |
| WO | 2005108361 A1 | 11/2005 |
| WO | 2006/100502 A1 | 9/2006 |
| WO | 2008106128 A2 | 9/2008 |

OTHER PUBLICATIONS

International Search Report and Written Opinion mailed Jun. 17, 2019 for PCT/CL2019/050029, 15 pp.
Database Registry [ online ], Chemical Abstracts Service, Columbus, Ohio, US. retrieved from STN, Jul. 20, 2016, RN 1955598-60-3.
Xia et al., "Design, synthesis and SAR of piperidyl oxadiazoles as 11 !3-hydroxysteroid dehydrogenase 1 inhibitors". European Journal of Medicinal Chemistry. Jan. 10, 2013, vol. 62, pp. 1-10, DOI: https://doi.org/10.1016/j.ejmech.2012.12 059.
Diethelm et al. "1-Adamantylamidoxime", Molbank 2018, Apr. 19, 2018, M992, p. 106.

*Primary Examiner* — Susanna Moore
(74) *Attorney, Agent, or Firm* — Fox Rothschild LLP (57) ABSTRACT

The present invention relates to compounds derived from adamantyl oxadiazoles and the pharmaceutically acceptable solvates, hydrates and salts of same. These compounds are suitable for use as effective and selective inhibitors of the reductase activity of the enzyme 11-beta dehydrogenase type 1 (11β-HSD1), as well as in the production of a drug for treating conditions and diseases such as high blood pressure, obesity, dyslipidaemia, type 2 diabetes, insulin resistance, glaucoma, metabolic syndrome, cognitive disorders, osteoporosis, immune disorders, depression and other conditions. Also provided is a pharmaceutical composition comprising the compounds and a method for preparing said composition.

6 Claims, 3 Drawing Sheets

DERIVATIVES OF ADAMANTYL OXADIAZOLES AND PHARMACEUTICALLY ACCEPTABLE SOLVATES, HYDRATES AND SALTS THEREOF, PHARMACEUTICAL COMPOSITION COMPRISING SAME, SYNTHESIS METHOD, SUITABLE FOR USE AS EFFECTIVE AND SELECTIVE INHIBITORS OF THE REDUCTASE ACTIVITY OF THE ENZYME 11-BETA DEHYDROGENASE TYPE 1 (11β-HSD1)

FIELD OF THE INVENTION

The present invention refers to compounds derived from adamantyl oxadiazoles and the solvates, hydrates and pharmaceutically acceptable salts thereof, as they are useful as effective and selective inhibitors of the reductase activity of the enzyme 11-beta hydroxysteroid dehydrogenase type 1 (11β-HSD1). In particular, the use of compounds derived from adamantyl oxadiazoles and their pharmaceutically acceptable salts is disclosed as being useful in the treatment of diseases and conditions related to the increase in cortisol mediated by the reductase activity of the enzyme 11β-HSD1. These diseases include, but are not limited to, high blood pressure, obesity, dyslipidaemia, type 2 diabetes, insulin resistance, glaucoma, metabolic syndrome, cognitive disorders, osteoporosis, depression, immune disorders, among other conditions. A process is also available to produce the compounds derived from adamantyl oxadiazoles.

BACKGROUND OF THE STATE OF THE ART

Glucocorticoids (GC) are steroid hormones linked to the regulation of various physiological and metabolic processes, such as the response to physical and emotional stress. These hormones produced by the adrenal cortex can be artificially synthesized and used as anti-inflammatory, antiallergic and immunosuppressant drugs derived from cholesterol or hydrocortisone.

The most important glucocorticoid molecule is cortisol, which is produced and released upon activation of the hypophyseal adrenal axis. This axis is activated after a period of stress, such as, for example, when exposed to physical aggression. When activated, the hypothalamus secretes the corticotropin releasing factor (CRF), which acts on the pituitary so that it releases the adenocorticotropic hormone (ACTH), which mediates the activation of the adrenal gland for the release of corticosteroids, among which is cortisol. Once in the bloodstream, cortisol remains bound to blood plasma proteins such as cortisol-binding globulin (CBG) and albumin, and the same circulates in its free form (10-15%) (Kadmiel M. and Cidlowski J A., 2013).

Once in the target tissue, the action and concentration of glucocorticoids depends on the 11-beta dehydrogenase enzyme system, which includes the enzymes 11-beta hydroxysteroid dehydrogenase type 1 (11β-HSD1) and type 2 (11β-HSD2). The isoform 1 is expressed mainly in the liver, vascular smooth muscles, adipose tissue, brain and pancreas, and isoform 2 is found mainly localized in the colon and kidney.

The enzyme 11β-HSD1 catalyzes the conversion of cortisone (physiologically inactive molecule) to cortisol through an oxide-reduction reaction dependent on the coenzyme NADPH. The reaction mediated by the enzyme 11β-HSD1 is a bidirectional reaction, acting as a hydroxysteroid reductase enzyme when it catalyzes the conversion of cortisone to cortisol, increasing intracellular levels of glucocorticoids. The enzyme is associated with the glucocorticoid receptor, allowing the cortisol produced to rapidly bind to the glucocorticoid receptor and exert its action.

According to previous studies, it was observed that murine models that have hepatic overexpression of the gene encoding the enzyme 11β-HSD1, have a phenotype of high blood pressure (increased blood pressure) and increased concentrations of the hormone aldosterone (Masuzaki H. et al. 2003). On the other hand, studies in rats with obese phenotype (Zucker rat) allow to conclude that, in obesity condition, there is an exacerbated activity of the hydroxysteroid reductase activity of the enzyme (Livingstone D E W. et al., 2000).

It was observed in vivo that the reductase hydroxysteroid action is predominant in the hepatic tissue, muscle and adipose tissue, promoting the conversion of cortisone to cortisol, significantly increasing the concentrations of glucocorticoids in these tissues. (Tomlinson J. W. et al, 2004).

Increasing the intracellular concentration of cortisol can lead to increased glucose production in the liver, promote increased adipocyte differentiation, and lead to insulin resistance. In this sense, the increase in cortisol concentrations at the intracellular level in tissues of metabolic importance was associated with the development of diseases such as obesity, diabetes, arterial hypertension, and metabolic syndrome, among others (Wake D. J. and Walker B. R., 2004; Walker B. R., 2006).

11β-HSD1 Enzyme Inhibitors

Various 11β-HSD1 enzyme inhibitor compounds have been previously described. Documents EP 1474139, WO/2006/000371, WO/2006/024628, US20090227631, EP1814846, U.S. Pat. No. 8,188,288, EP1801098, WO/2007/068330, EP2044004, WO/2007/145835, WO/2007/145835, WO/2008/052638, EP1935420, U.S. Pat. No. 7,329,683, WO 2010139827 A1, EP1918285, US20100069365, US20100022597, US20100222316 A1 are only examples of documents referring to inhibitor compounds of this enzyme.

Document WO/2006/100502 discloses compounds of formula (I): $R^1$—Z—$R^2$ as being useful as inhibitors of the enzyme 11β-HSD1. In one of the forms of the invention, the compound of formula (I) corresponds to a derivative of adamantyl oxadiazole, however, this compound additionally includes in its structure a thiophene group, being structurally different from the compounds that are part of the scope of the present invention.

Despite the existence of various inhibitory compounds for the 11β-HSD1 enzyme, the previously described compounds focus their mechanism of action and selectivity with respect to isoforms 1 and 2 of the 11β-HSD1 enzyme, aiming to completely inhibit the action of isoform 1, without discriminating the type of enzymatic reaction (action as reductase or as dehydrogenase). Document WO 2006000371 A2, for example, presents compounds derived from pyrimidine as inhibitors of the enzyme 11β-HSD1 which have selective activity against isoform 2 of the enzyme, without referring to the selectivity of the inhibitor with respect to the reductase or dehydrogenase (oxidase) action of the 11β-HSD1 enzyme.

The inhibitors described in the present application show inhibitory activity on the reductase action of the enzyme 11β-HSD1, increase its oxidase activity, and, at the same time, do not inhibit the action of the enzyme 11β-HSD2.

On the other hand, the inventors have identified new inhibitory compounds that, in addition to being specific and selective for the activities of the 11β-HSD1 enzyme, achieve the desired therapeutic effect with lower concentrations than those used for other inhibitory drugs. For example, document WO2006100502 A1 presents the information on the inhibition of the compounds described therein, which are effective at doses of 10 µM. The compounds of formula (I) described in the present application show inhibitory activity with doses of the order nM (100 nM).

In short, the compounds of formula (I) show inhibitory activity of the enzyme 11β-HSD1 in a selective and specific way due to its reductase activity, using less concentrations to generate the desired therapeutic effect.

DETAILED DESCRIPTION OF THE INVENTION

The present invention refers to compounds of the adamantyl oxadiazole type of formula (I) and the solvates, hydrates and pharmaceutically acceptable salts thereof:

because L is independently selected from a carbon or nitrogen atom, $R_1$, $R_2$ and $R_3$ are independently selected from a hydrogen atom, F, Br, Cl, $NO_2$, a linear or branched Ca alkyl group, or an OR group, where R is H or a linear or branched $C_{1-4}$ alkyl group.

Examples of preferred compounds of formula (I) are:

1-phenyl-2-(3-adamantyl-1,2,4-oxadiazol-5-yl)ethane

BD-31

1-(4-Methoxyphenyl)-2-(3-adamantyl-1,2,4-oxadiazol-5-yl)ethane

BD-32

1-(4-chlorophenyl)-2-(3-adamantyl-1,2,4-oxadiazol-5-yl)ethane

BD-33

1-(4-fluorophenyl)-2-(3-adamantyl-1,2,4-oxadiazol-5-yl)ethane

BD-34

1-(4-bromophenyl)-2-(3-adamantyl-1,2,4-oxadiazol-5-yl)ethane

BD-35

BD-36

1-(4-methylphenyl)-2-(3-adamantyl-
1,2,4-oxadiazol-5-yl)ethane

BD-37

1-(4-hydroxyphenyl)-2-(3-adamantyl-
1,2,4-oxadiazol-5-yl)ethane

BD-38

1-(3-methoxyphenyl)-2-(3-adamantyl-
1,2,4-oxadiazol-5-yl)ethane

BD-39

1-(4-pyridyl)-2-(3-adamantyl-1,2,4-
oxadiazol-5-yl)ethane

BD-40

1-(3-methylphenyl)-2-(3-adamantyl-
1,2,4-oxadiazol-5-yl)ethane

BD-41

1-(4-tert-butylphenyl)-2-(3-adamantyl-
1,2,4-oxadiazol-5-yl)ethane

BD-42

1-(3-fluorophenyl)-2-(3-adamantyl-
1,2,4-oxadiazol-5-yl)ethane

BD-44

1-(3-pyridyl)-2-(3-adamantyl-1,2,4-
oxadiazol-5-yl)ethane 1-(2-pyridyl)-2-(3-adamantyl-1,2,4-oxadiazol-5-yl)ethane

BD-45

1-(4-nitrophenyl)-2-(3-adamantyl-1,2,4-oxadiazol-5-yl)ethane

BD-46

The object of the present invention is to provide new inhibitor compounds of the enzyme 11-beta dehydrogenase type 1. In particular, the inventors have identified, synthesized and characterized compounds of the adamantyl oxadiazole type that have comparative advantages with respect to other inhibitor compounds of the enzyme 11β-HSD1 as to its specificity for the reductase activity of the enzyme and its selectivity with respect to isoforms 1 and 2 (11β-HSD2). In this sense, the compounds described in the present application show inhibitory activity on the reductase action of the 11β-HSD1 enzyme, increase its oxidase activity, and, at the same time, do not affect the action of the 11β-HSD2 enzyme.

The inventors have identified new specific and selective inhibitor compounds of the reductase activity of the enzyme 11β-HSD1 in such a way as to achieve the desired therapeutic effect by means of concentrations on the order of μM.

The compounds of formula (I) part of the scope of the invention, include both their unsolvated forms and solvated forms, including their hydrates, for example, hemihydrates.

It is also an object of the present invention to have pharmaceutically acceptable compositions comprising compounds of the adamantyl oxadiazole type of formula (I).

The scope of the present invention includes the use of compounds of formula (I), their pharmaceutically acceptable salts, solvates and hydrates, and pharmaceutically acceptable compositions comprising them, for being useful as selective inhibitors of the 11β-HSD1 enzyme. Additionally, the use of compounds of formula (I), their pharmaceutically acceptable salts, solvates and hydrates, and pharmaceutically acceptable compositions comprising them, are disclosed as being useful in the preparation of a drug for the treatment of conditions and diseases associated with the 11β-HSD1 enzyme activity, such as high blood pressure, obesity, dyslipidaemia, type 2 diabetes, insulin resistance, glaucoma, metabolic syndrome, cognitive disorders, osteoporosis, depression, immune disorders, among other conditions.

The present invention further includes a process for preparing the compounds derived from adamantyl oxadiazoles.

DEFINITIONS

In the present invention, when referring to pharmaceutically acceptable salts, non-toxic salts, prepared from the addition of a base or acid suitable for administration in mammals, in particular humans, are included. Pharmaceutically acceptable salts include salts derived from the addition of pharmaceutically acceptable inorganic or organic bases, and pharmaceutically acceptable inorganic or organic acids.

Salts derived from pharmaceutically acceptable acids include, but are not limited to, acetic, benzoic, benzene sulfonic, camphorsulfonic, citric, ethanesulfonic, fumaric, gluconic, glutamic, hydrobromic, hydrochloric, lactic, maleic, malic, mandelic, methanesulfonic, mucus, nitric, pantothenic, phosphoric, succinic, sulfuric, tartaric, p-toluenesulfonic, xinafoic acids and the like. Particularly preferred salts are salts derived from fumaric, hydrobromic, hydrochloric, acetic, sulfuric, methanesulfonic, xinafoic and tartaric acids.

Salts derived from the addition of pharmaceutically acceptable inorganic bases include, but are not limited to, salts of aluminum, ammonium, calcium, sodium, zinc, and the like. Ammonium, calcium, magnesium, potassium and sodium salts are preferred.

Salts derived from the addition of pharmaceutically acceptable organic bases include, but are not limited to, salts of primary, secondary and tertiary amines, including substituted amines, cyclic amines, naturally occurring amines, and the like, such as, arginine, betaine, caffeine, choline N,N'-dibenzylethylenediamine, diethylamine, 2-diethylaminoethanol, 2-dimethylaminoethanol, ethanolamine, ethylenediamine, N-ethylmorpholine, N-ethylpiperidine, glucosamine, histidine, isopropylamine, lysine, methylglucamine, morpholine, piperazine, resin, polyamine resins, procaine, purines, theobromine, triethylamine, trimethylamine, tripropylamine, tromethamine, and the like.

In the present invention, when referring to solvates, including hydrates or other types of solvates, these are formed from the contact of the unsolvated form of compounds of formula (I) and their pharmaceutically acceptable salts with a solvent. Representative solvents include, but are not limited to, water, ethanol, methanol, isopropanol, acetic acid, and the like. In particular, when the solvent corresponds to water, the solvate formed is a hydrate.

When referring to "disease or conditions associated with the activity of the enzyme 11β-HSD1," all disease states and/or states that are currently recognized or that will be in the future linked to increased activity of the enzyme 11β-HSD1, and therefore, to the increase in tissue cortisol levels, are being considered. The diseases and conditions described include, but are not limited to, high blood pressure, obesity, dyslipidaemia, type 2 diabetes, insulin resistance, metabolic syndrome, glaucoma, osteoporosis, cognitive disorders, depression, anxiety, immune disorders, and similar conditions associated with increased cortisol levels produced by the enzyme 11β-HSD1.

The term "therapeutically effective amount" refers to an amount sufficient to effect treatment when administered to a patient in need of treatment.

In the present invention, when reference is made to "treatment," it refers to the treatment of a disease, pathological condition or medical condition in a human patient that includes:

(a) preventing the development of the disease or condition as a prophylactic treatment of the patient;
(b) alleviating the disease or condition, causing its regression;
(c) suppressing the disease or medical condition, slowing down the degree of its development in a patient; or
(d) decreasing or alleviating the symptoms associated with the disease or medical condition in a patient.

APPLICATION EXAMPLES

Example 1: Synthesis and Characterization of Compounds of Formula (I)

This example presents the chemical synthesis of the parent compound for the synthesis of compounds of formula (I) that are part of the present invention, and the synthesis of examples of new compounds derived from adamantyl oxadiazoles of formula (I) that are part of its scope.

Synthesis and Characterization of the Adamantylamidoxime Parent Compound (1)

1

A mixture of hydroxylamine hydrochloride (2.59 g, 37.2 mmol) and sodium carbonate (3.93 g. 37.1 mmol) was prepared in ethanol (10 mL) and glycerol (10 mL), which was stirred overnight at room temperature. Then, a solution of cyanoadamantane (2.00 g, 12.4 mmol) and aluminum chloride (0.25 g, 1.86 mmol) in ethanol (30 mL) was prepared, stirred for 30 min at room temperature, and added dropwise to the hydroxylamine-carbonate mixture. The resulting white suspension was vigorously stirred under reflux conditions for 10 hrs. The progress of the reaction was monitored by TLC using iodine vapor as the developer. After 10 hrs, the residual ethanol was removed by vacuum filtration. The residue is partitioned with water and dichloromethane, and the aqueous phase is further extracted with dichloromethane. The resulting organic phase was washed with brine and dried over anhydrous sodium sulfate, yielding a white product. This white product was purified by recrystallization using an acetone-hexane mixture, generating colorless crystals corresponding to adamantylamidoxime (1). The synthesis yield was 85%. Compound melting point (1): 210-215° C. IR (KBr) cm$^{-1}$: 3505 (N—H), 3405 (free O—H), 3218 (H-bonded O—H), 2908-2850 (C—H sp3): 1645 (C=N). 1582 (NH2), 1454 (CH2), 1357 (C—N). $^1$H-NMR (ppm) (400 MHz, CDCl3) δ: 4.51 (s, 2H, —NH2); 1.98 (bs, 6H, H-1): 1.80 (bs, 3H, H-2); 1.67 (m, 6H, H-3). $^{13}$C-NMR (ppm) (101 MHz, CDCl3) δ: 159.6; 39.7; 36.6; 36.5; 28.1. Calculated molecular mass: 194.1419 g/mol; Observed molecular mass: 194.1413 g/mol.

Synthesis and Characterization of Compound BD-31: 1-phenyl-2-(3-adamantyl-1,2,4-oxadiazol-5-yl)ethane A solution of 2-chloro-4,6-dimethoxy-1,3,5-triazine (497 mg. 2.83 mmol) in 1,4-dioxane (10 mL) was prepared and stirred at room temperature. N-methylmorpholine (849 μL, 7.72 mmol) was added dropwise and the mixture was stirred for 5 min at room temperature. Next, a solution of 3-phenylpropionic acid (425 mg, 2.83 mmol) in 1,4-dioxane (5 mL) was added, and the resulting mixture was stirred for 30 min at room temperature. Then, a solution of the adamantylamidoxime parent compound (1) (500 mg, 2.57 mmol) in 1,4-dioxane (5 mL) was added and the resulting mixture was vigorously stirred under reflux conditions for 3 hrs. The progress of the reaction was monitored by TLC. After 3 hrs, the mixture was cooled to room temperature and a 5% sodium carbonate solution was added. The product was extracted with dichloromethane. The organic phase was dried over anhydrous sodium sulfate and the solvent was removed by vacuum.

The resulting crude product was purified by gravity column chromatography using a mixture of 10% ethyl acetate in n-hexane as eluent. As an additional purification step, the product was purified by thin layer chromatography using n-hexane as eluent, obtaining a colorless gel. Melting point: product in gel state. IR (KBr) cm$^{-1}$: 3086-3028 (=C—H sp$^2$ Ar), 2917-2850 (C—H sp$^3$), 1579 (C=N), 1497 (C=C Ar), 1453 (CH$_2$), 1349 (C—N), 1304-1026 (C—O). $^1$H-NMR (ppm) (400 MHz, CDCl$_3$) δ: 7.31 (dd, 2H, H-1"); 7.23 (dd, 3H, H-2", H-3"); 3.16 (in, 4H, H-1', H-2'); 2.07 (m, 9H, H-1, H-2); 1.81 (bs, 6H, H-3). $^{13}$C-NMR (ppm) (101 MHz, CDCl$_3$) δ: 178.2; 177.0; 139.6; 128.6; 128.3; 126.6; 40.2; 36.5; 34.3; 32.8; 28.6; 28.0. Calculated molecular mass: 308.1889 g/mol; Observed molecular mass: 308.1883 g/mol.

Synthesis and Characterization of Compound BD-32: 1-(4-methoxyphenyl)-2-(3-adamantyl-1,2,4-oxadiazol-5-yl)ethane Prepared from 2-chloro-4,6-dimethoxy-1,3,5-triazine (248 mg, 1.42 mmol), N-methylmorpholine (424 μL, 3.87 mmol), 3-(4-methoxyphenyl) propionic acid (255 mg), 1.42 mmol) and parent compound (1) (250 mg, 1.29 mmol). A crude product was obtained, which was purified by gravity column chromatography using a mixture of 10% ethyl acetate in n-hexane as eluent, yielding a white solid. The reaction yield was 42%. Melting point: 48-53° C. IR (KBr) cm$^{-1}$: 3066-3003 (=C—H sp$^2$ Ar), 2908-2850 (C—H sp$^3$), 1588 (C=N), 1612 (C=C Ar), 1451 (CH$_2$), 1391 (CH$_3$), 1346 (C—N), 1301 (C—O). $^1$H-NMR (ppm) (400 MHz, CDCl$_3$) δ: 7.24 (d, J=8.0 Hz, 2H, H-1"); 6.96 (d, J=8.1 Hz, 2H, H-2"); 3.90 (s, 3H, —OCH$_3$); 3.22 (in, 4H, H-1', H-2'); 2.19 (in, 9H, H-1, H-2); 1.93 (bs, 6H, H-3). BC-NMR (ppm) (101 MHz, CDCl$_3$) δ: 178.3; 176.9; 158.3; 131.6; 129.2; 114.0; 55.2; 40.2; 36.5; 34.2; 31.9; 28.8; 28.0. Calculated molecular mass: 338.5 g/mol. Observed molecular mass: 338.3 g/mol.

Synthesis and Characterization of Compound BD-33: 1-(4-chlorophenyl)-2-(3-adamantyl-1,2,4-oxadiazol-5-yl)ethane A mixture of 2-chloro-4,6-dimethoxy-1,3,5-triazine (497 mg, 2.83 mmol), N-methylmorpholine (849 μL, 7.72 mmol), 3-(4-chlorophenyl) propionic acid (523 mg, 2.83 mmol) and the adamantylamidoxime parent compound (1) (500 mg, 2.57 mmol) was prepared, obtaining a product that was purified by means of gravity column chromatography using a mixture of acetate 10% ethyl in n-hexane as eluent. As a further purification step, the product was purified by recrystallization from ethanol to provide a white solid. The reaction yield was 69%. Melting point: 78-83° C. IR (KBr) cm$^{-1}$: 3065-3026 (=C—H sp$^2$ Ar), 2908-2848 (C—H sp$^3$), 1582 (C=N), 1495 (C=C Ar), 1453 (CH$_2$), 1349 (C—N), 1305-1014 (C—O), 1094 (C—Cl Ar). $^1$H-NMR (ppm) (400 MHz, CDCl$_3$) δ: 7.24 (d, J=7.9 Hz, 2H, H-2"); 7.11 (d, J=7.8 Hz, 2H, H-1"); 3.10 (m, 4H, H-1', H-2'); 2.03 (m, 9H, H-1, H-2): 1.77 (bs, 6H, H-3). $^{13}$C-NMR (ppm) (101 MHz, CDCl$_3$) δ: 177.9; 177.0; 137.9; 132.5; 129.7; 128.8; 40.2; 36.5; 34.2; 32.0; 28.4; 28.0. Calculated molecular mass: 342.1499 g/mol; Observed molecular mass: 342.1496 g/mol.

Synthesis and Characterization of Compound BD-34: 1-(4-fluorophenyl)-2-(3-adamantyl-1,2,4-oxadiazol-5-yl)ethane This compound was prepared from the reaction of 2-chloro-4,6-dimethoxy-1,3,5-triazine (248 mg, 1.42 mmol), N-methylmorpholine (424 μL, 3.86 mmol), 3-(4-fluorophenyl) propionic acid (216 mg), 1.29 mmol) and 1 (300 mg, 1.54 mmol) to provide a crude product, which was purified by gravity column chromatography using a mixture of 20% ethyl acetate in n-hexane as eluent, providing a white solid. The reaction yield was 56%. Melting point: 62-64° C. IR (KBr) cm–1: 3064-3005 (=C—H sp$^2$ Ar), 2905-2848 (C—H sp$^3$), 1579 (C=N), 1604 (C=C Ar), 1453 (CH$_2$), 1348 (C—N), 1303-1026 (C—O), 1256-1088 (C—F Ar). $^1$H-NMR (ppm) (400 MHz, CDCl$_3$) δ: 7.41 (dd, 2H, H-1"); 7.23 (dd. 2H, H-2'): 3.38 (m, 4H, H-1', H-2'); 2.31 (m, 9H, H-1, H-2): 2.05 (bs, 6H, H-3). BC-NMR (ppm) (101 MHz, CDCl$_3$) δ: 178.0; 177.0; 161.7 (d, J=244.7 Hz, 1C); 135.2 (d, J=3.3 Hz, 1C): 129.8 (d, J=7.9 Hz, 2C); 115.4 (d, J=21.3 Hz, 1C); 40.2; 36.5; 34.2; 31.9; 28.7; 28.0. Calculated molecular mass: 326.4 g/mol; Observed molecular mass: 326.4 g/mol.

Synthesis and Characterization of Compound BD-35: 1-(4-bromophenyl)-2-(3-adamantyl-1,2,4-oxadiazol-5-yl)ethane For this synthesis, a mixture containing 2-chloro-4,6-dimethoxy-1,3,5-triazine (273 mg, 1.56 mmol), N-methyl-morpholine (424 μL, 3.86 mmol), 3-(4-Bromophenyl) propionic acid (324 mg, 1.42 mmol) and the parent compound adamantylamidoxime (1) (325 mg, 1.67 mmol) was prepared to give a product that was purified by gravity column chromatography using a mixture of 10% ethyl acetate in n-hexane as eluent.

From purification, a white solid was obtained. The reaction yield was 69%. Melting point: 95-100° C. IR (KBr) cm–1: 3063-3022 (=C—H sp$^2$ Ar), 2908-2846 (C—H sp$^3$), 1580 (C=N), 1491 (C=C Ar), 1451 (CH$_2$), 1348 (C—N), 1304-1010 (C—O), 1072 (C—Br Ar). $^1$H-NMR (ppm) (400 MHz, CDCl3) δ: 7.41 (d, J=8.1 Hz, 2H, H-2"); 7.22 (d, J=8.0 Hz, 2H, H-1"); 3.11 (sa, 4H, H-1', H-2'); 2.05 (m, 9H, H-1, H-2); 1.79 (bs, 6H, H-3). $^{13}$C-NMR (ppm) (101 MHz, CDCl$_3$) δ: 177.8; 177.0; 138.5; 131.7; 130.1; 120.5; 40.2; 36.5; 34.2; 32.1; 28.3; 27.9. Calculated molecular mass: 386.0994 g/mol; Observed molecular mass: 386.0989 g/mol.

Synthesis and Characterization of Compound BD-36: 1-(4-methylphenyl)-2-(3-adamantyl-1,2,4-oxadiazol-5-yl)ethane A mixture of 2-chloro-4,6-dimethoxy-1,3,5-triazine (273 mg, 1.56 mmol), N-methylmorpholine (466 μL, 4.23 mmol), 3-(p-tolyl) propionic acid (232 mg, 1.42 mmol) and the parent compound adamantylamidoxime (1) (302 mg, 1.56 mmol) was prepared to obtain a product that was purified by gravity column chromatography using a mixture of ethyl acetate 10% in n-hexane as eluent. As a further purification step, the product was recrystallized from ethanol to provide a white solid. The production yield of the compound was 58%. Melting point: 64-68° C. IR (KBr) cm$^{-1}$ 3064-3017 (=C—H sp$^2$ Ar), 2905-2849 (C—H sp$^3$), 1584 (C=N), 1516 (C=C Ar), 1452 (CH$_2$), 1387 (CH$_3$), 1348 (C—N), 1305-1087 (C—O). $^1$H-NMR (ppm) (400 MHz, CDCl$_3$) δ: 7.23 (bs, 4H, H-1", H-2"); 3.24 (m, 4H, H-1', H-2'); 2.45 (s, 3H, —CH$_3$); 2.19 (m, 9H, H-L, H-2); 1.92 (bs, 6H, H-3). $^{13}$C-NMR (ppm) (101 MHz, CDCl$_3$) δ: 178.3; 177.0; 136.5; 136.1; 129.3; 128.2; 40.2; 36.5; 34.3; 32.4; 28.8; 28.0; 21.0. Calculated molecular mass: 322.2045 g/mol; Observed molecular mass: 322.2040 g/mol.

Synthesis and Characterization of Compound BD-37: 1-(4-hydroxyphenyl)-2-(3-adamantyl-1,2,4-oxadiazol-5-yl)ethane Prepared from 2-chloro-4,6-dimethoxy-1,3,5-triazine (237 mg, 1.56 nmol), N-methylmorpholine (466 μL, 4.25 mmol), 3-(4-hydroxyphenyl) propionic acid (235 mg, 1.42 mmol) and 1 (302 mg, 1.56 mmol) to give a crude product, which was purified by gravity column chromatography using a mixture of 20% ethyl acetate in n-hexane as eluent, providing a pale yellow gel. Yield: 70%; Melting point: product in gel state. IR (KBr) cm–1: 3409 (OH bound to H), 3042 (=CH sp$^2$ Ar), 2903-2848 (CH sp3), 1664-1516 (C=C Ar), 1574 (C=N), 1452 (CH2), 1350 (CN), 1305-1026 (heterocyclic CO), 1227 (phenolic CO). $^1$H-NMR (ppm) (400 MHz, CDCl3): 7.01 (d, J=8.3 Hz, 2H, H-1'): 6.75 (d, J=8.4 Hz, 2H, H-2"); 3.08 (m, 4H, H-1H-2'): 2.05 (in, 9H, H-1. H-2); 1.78 (bs, 6H, H-3). $^{13}$C-NMR (ppm) (101 MHz, CDCl3): 178.6; 176.9; 154.7; 131.2; 129.4; 115.6; 40.1; 36.4; 34.3; 31.9; 28.9; 27.9. Calculated molar mass: 324.4 g/mol. Found molar mass: 324.3 g/mol.

Synthesis and Characterization of Compound BD-38: 1-(3-methoxyphenyl)-2-(3-adamantyl-1,2,4-oxadiazol-5-yl)ethane This compound is prepared from the reaction of 2-chloro-4,6-dimethoxy-1,3,5-triazine (268 mg, 1.53 mmol), N-methylmorpholine (458 µL, 4.16 mmol), 3-(3-methoxyphenyl) propionic acid (250 mg), 1.39 mmol) and 1 (296 mg, 1.53 mmol) to give a crude product, which was purified by gravity column chromatography using a mixture of 20% ethyl acetate in n-hexane as eluent, providing a colorless gel. The yield of the compound was 48%. Melting point: product in gel state. $^1$H-NMR (ppm) (400 MHz, CDCl$_3$) δ: 7.23 (t, J=7.7 Hz, 1H, H-2"); 6.80 (m, 3H, H-1", H-3", H-4"); 3.81 (s, 3H, —OCH$_3$); 3.14 (m, 4H, H-1', H-2'); 2.08 (m, 9H, H-1, H-2); 1.81 (bs, 6H, H-3). $^{13}$C-NMR (ppm) (101 MHz, CDCl$_3$) δ: 178.2; 177.0; 159.8; 141.2; 129.6; 120.6; 114.0; 112.1; 55.2; 40.2; 36.5; 34.3; 32.8; 28.5; 28.0.

Synthesis and Characterization of Compound BD-39: 1-(4-pyridyl)-2-(3-adamantyl-1,2,4-oxadi-azol-5-yl)ethane A reaction mixture was prepared comprising 2-chloro-4,6-dimethoxy-1,3,5-triazine (319 mg, 1.82 mmol), N-methylmorpholine (546 µL, 4.96 mmol), 3-(4-pyridyl) propionic acid (250 mg, 1.65 mmol) and the parent compound (1) (354 mg, 1.82 mmol). From this reaction, a product was obtained which was purified by means of gravity column chromatography using a mixture of 40% ethyl acetate in n-hexane as eluent. As an additional purification step, the product was purified by thin layer chromatography using n-hexane as eluent, obtaining a yellow solid. The synthesis yield was 52%. Melting point: 75-78° C. IR (KBr) cm−1: 2909-2847 (C—H sp$^3$), 1574 (C=N), 1512 (C=C Ar), 1451 (CH$_2$), 1343 (C—N), 1303-1088 (C—O), 810 (C=N). $^1$H-NMR (ppm) (400 MHz, CDCl$_3$) δ: 8.1 (d, J=4.4 Hz, 2H, H-1"); 7.24 (d, J=4.5 Hz, 2H, H-2"); 3.25 (m, 4H, H-1', H-2'): 2.13 (m, 9H, H-1, H-2); 1.87 (bs, 6H, H-3). $^{13}$C-NMR (ppm) (101 MHz, CDCl$_3$) δ: 177.4; 177.1; 149.8; 148.5; 123.7; 40.2; 36.5; 34.3; 31.8; 27.9:27.2. Calculated molecular mass: 309.1841; Observed molecular mass: 309.1834.

Synthesis and Characterization of Compound BD-40: 1-(3-methylphenyl)-2-(3-adamantyl-1,2,4-oxadiazol-5-yl)ethane This compound is prepared from the reaction of 2-chloro-4,6-dimethoxy-1,3,5-triazine (276 mg, 1.57 mmol), N-methylmorpholine (472 µL, 4.29 mmol), 3-(3-methylphenyl) propionic acid (235 mg, 1.43 mmol) and 1 (333 mg, 1.71 mmol) to provide a crude product, which was purified by gravity column chromatography using a mixture of 30% ethyl acetate in n-hexane as eluent. As an additional purification step, the product was purified by preparative thin layer chromatography using n-hexane as eluent to provide a colorless gel. The yield of this synthesis reaction was 96%. Melting point: 58-60° C. IR (KBr) cm−1: 3032(=C—H sp$^2$ Ar), 2909-2847 (C—H sp$^3$), 1582 (C=N), 1512 (C=C Ar), 1443 (CH$_3$), 1389 (CH$_3$), 1342 (C—N), 1296-1088 (C—O). $^1$H-NMR (ppm) (400 MHz, CDCl$_3$) δ: 7.39 (t, J=7.2 Hz, 1H, H-2"): 7.23 (m, 3H, H-1", H-3", H-4"); 3.32 (m, 4H, H-1', H-2'); 2.54 (s, 3H, —CH$_3$): 2.27 (m, 911, H-1, H-2); 2.00 (bs, 6H, H-3). $^{13}$C-NMR (ppm) (101 MHz, CDCl$_3$) δ: 178.3; 177.0; 139.5; 138.2; 129.1; 128.5; 127.3; 125.3; 40.2; 36.5; 34.3; 32.7; 28.7; 28.0; 21.4. Calculated molecular mass: 322.2045 g/mol; Observed molecular mass: 322.2024 g/mol.

Synthesis and Characterization of Compound BD-41 1-(4-tert-butylphenyl)-2-(3-adamantyl-1,2,4-oxadiazol-5-yl)ethane The synthesis was carried out by preparing a reaction mixture composed of 2-chloro-4,6-dimethoxy-1,3,5-triazine (234 mg, 1.33 mmol), N-methylmorpholine (400 µL, 3.64 mmol), 3-(4-tert-butylphenyl) propionic acid (250 mg, 1.21 nmol) and parent compound (1) (282 mg, 1.45 mmol). From this reaction, a product was obtained which was purified by gravity column chromatography using a mixture of 10% ethyl acetate in n-hexane as eluent. As a further purification step, the product was recrystallized from ethanol to provide a white solid. The yield of this synthesis was 80%. Melting point: 88-91° C. IR (KBr) cm$^{−1}$: 2909-2855 (C—H sp$^3$), 1574 (C=N), 1504 (C=C Ar), 1450 (CH$_2$), 1358 (CH$_3$), 1343 (C—N), 1296-1088 (C—O). $^1$H-NMR (ppm) (400 MHz. CDCl$_3$) δ: 7.51 (m, 1H, H-3"); 7.22 (d, J=7.7 Hz, 1H, H-4"): 7.17 (m, 2H, H-1", H-2"); 3.39 (m, 4H, H-1', H-2'); 2.30 (in, 9H, H-1, H-2); 2.04 (bs, 6H, H-3). $^{13}$C-NMR (ppm) (101 MHz, CDCl3) δ: 177.8; 177.1; 162.9 (d, J=$^2$46.0 Hz. 1C): 142.0 (d, J=7.3 Hz, 1C); 130.1 (d, J=8.4 Hz, 1C); 123.9 (d, J=2.8 Hz, 1C); 115.3 (d, J=21.3 Hz, 1C); 113.6 (d, J=21.0 Hz, 1C); 40.2; 36.5; 32.4; 28.3; 28.0. Calculated molecular mass: 364.2515 g/mol; Observed molecular mass: 364.2509.

Synthesis and Characterization of BD-42 compound 1-(3-fluorophenyl)-2-(3-adamantyl-1,2,4-oxadiazol-5-yl)ethane Prepared from the reaction of 2-chloro-4,6-dimethoxy-1,3,5-triazine (mg, mmol), N-methylmorpholine (L, mmol), 3-(3-fluorophenyl) propionic acid (mg, mmol) and 1 (mg, mmol) to give a crude product, which was purified by gravity column chromatography using a mixture of 10% ethyl acetate in n-hexane as eluent, providing a colorless gel. The yield of this synthesis was 56%. Melting point: product in gel state. $^1$H-NMR (ppm) (400 MHz. CDCl$_3$) δ: 7.51 (m. 1H, H-3"). 7.22 (d, J=7.7 Hz, 1H, H-4"): 7.17 (m, 2H, H-1", H-2"); 3.39 (m, 4H, H-1', H-2'); 2.30 (in, 9H, H-1, H-2); 2.04 (bs, 6H, H-3). $^{13}$C-NMR (ppm) (101 MHz. CDCl$_3$) δ: 177.8; 177.1; 162.9 (d, J=246.0 Hz, 1C); 142.0 (d, J=7.3 Hz, 1C): 130.1 (d, J=8.4 Hz, 1C); 123.9 (d, J=2.8 Hz, 1C); 115.3 (d, J=21.3 Hz, 1C); 113.6 (d, J=21.0 Hz, 1C); 40.2; 36.5; 32.4; 32.4; 28.3; 28.0.

Synthesis and Characterization of Compound BD-44: 1-(3-pyridyl)-2-(3-adamantyl-1,2,4-oxadi-azol-5-yl)ethane The synthesis was carried out from a mixture of 2-chloro-4,6-dimethoxy-1,3,5-triazine (226 mg, 1.29 mmol), N-methylmorpholine (386 µL, 3.51 mmol), 3-(3-pyridyl) propionic acid (177 mg. 1.17 mmol) and the parent compound (1) (250 mg, 1.29 mmol). From the mixture, a product was obtained which was purified by gravity column chromatography using a mixture of 40% ethyl acetate in n-hexane as eluent. Additionally, another purification step was carried out by means of thin layer chromatography using n-hexane as eluent, obtaining a yellow gel as a product. The yield of this synthesis reaction was 44%. Melting point: Product in gel state. $^1$H-NMR (ppm) (400 MHz. CDCl$_3$) δ: 8.61 (bs, 2H, H-2", H-3"); 7.77 (d, J=7.7 Hz, 1H, H-4"); 7.43 (s, 1H, H-1"); 3.18 (bs, 4H, H-1', H-2'); 1.99 (in, 9H, H-1, H-2); 1.73 (bs, 6H, H-3). $^{13}$C-NMR (ppm) (101 MHz, CDCl$_3$) δ: 177.4; 177.0; 149.1; 147.5; 136.6; 135.3; 123.7; 40.1; 39.6; 36.5; 34.2; 29.7; 27.9.

Synthesis and Characterization of Compound BD-45: 1-(2-pyridyl)-2-(3-adamantyl-1,2,4-oxadi-azol-5-yl)ethane Prepared from 2-chloro-4,6-dimethoxy-1,3,5-triazine (226 mg, 1.17 mmol), N-methylmorpholine (386 µL, 3.51 mmol), 3-(2-pyridyl) propionic acid (177 mg), 1.17 mmol) and 1 (250 mg, 1.287 mmol) to give a crude product, which was purified by gravity column chromatography using a mixture of 60% ethyl acetate in n-hexane as eluent. As an additional purification step, the product was purified by preparative thin layer chromatography using n-hexane as eluent to provide a yellow gel. The yield of this synthesis reaction was 18%. Melting point: Product in gel state. $^1$H-NMR (ppm) (400 MHz, CDCl$_3$) δ: 8.54 (d. J=7.2 Hz, 1H, H-1"): 7.69 (m, 1H, H-3"); 7.23 (in, 2H, H-2", H-4"); 3.26 (m, 4H, H-1', H-2'); 1.87 (in, 9H, H-1, H-2); 1.62 (bs, 6H, H-3). $^{13}$C-NMR (ppm) (101 MHz, CDCl$_3$) δ: 177.6; 177.0; 159.6; 147.2; 139.5; 122.9; 40.1; 36.5; 34.2; 32.9; 27.9; 26.0.

Synthesis and Characterization of Compound BD-46: 1-(4-nitrophenyl)-2-(3-adamantyl-1,2,4-oxadiazol-5-yl)ethane Prepared from the reaction of 2-chloro-4,6-dimethoxy-1,3,5-triazine (226 mg, 1.29 mmol), N-methylmorpholine (386 µL, 3.51 mmol), 3-(4-nitrophenyl) propionic acid (228 mg, 1.17 mmol) and 1 (250 mg, 1.29 mmol) to give a crude product, which was purified by gravity column chromatography using a mixture of ethyl acetate at 20% in n-hexane as eluent, yielding a white solid. The yield of this synthesis reaction was 66%. $^1$H-NMR (ppm) (400 MHz, CDCl$_3$) δ: 8.00 (d, J=8.6 Hz, 2H, H-1"): 7.22 (d, J=8.5 Hz, 2H, H-2"): 3.08 (in, 4H, H-1', H-2'); 1.89 (m, 9H, H-1, H-2): 1.63 (bs, 6H, H-3). $^{13}$C-NMR (ppm) (101 MHz. CDCl$_3$) δ: 177.3; 177.1; 147.0; 146.9; 129.3; 123.9; 40.2; 36.5; 34.3; 32.3; 27.9; 27.8.

Example 2: Inhibitory and Selective Effect of Compounds of Formula (I) on the Activity of the Enzyme 11β-HSD1

In this example, biological activity assays are presented to determine the inhibitory effect of compounds of formula (I) against the enzyme 11β-HSD1 dehydrogenase and how these compounds specifically inhibit the oxidase (dehydrogenase) activity of the enzyme and its selectivity with respect to isoforms 1 and 2 (11β-HSD2).

The biological activity assays are performed by determining the 50% inhibitory concentration (IC50) of cortisol production with respect to the control when a recombinant enzyme 11β-HSD1 (Cayman Chemical, MI, USA; Item No. 10007815) is exposed to the different compounds.
Determination of 11β-HSD1 Reductase Activity First, stock solutions of the compounds were prepared in DMSO at a concentration of 10 µM, of which serial dilutions were made in order to determine the efficacy curve.

As for the recombinant 11β-HSD1 enzyme (Cayman Chemical, MI, USA; Item No. 10007815), it was prepared in Tris Buffer 20 mM EDTA 5 mM pH 6.0 (Tris buffer) at different dilutions.

Initially, the enzyme concentration to be used in the assays in order to evaluate the biological activity of the compounds was determined. The Cortisol Kit product (Cisbio, MA, USA; Cat no. 62CRTPEG) was used for that purpose.

The protocol consisted of preparing the reaction buffer, adding 266 nM cortisone and 333 µM NADPH in Tris buffer. Then, this reaction buffer is added to the wells of the HTRF (Homogeneous Time Resolved Fluorescence) reaction plate together with the enzyme in a 4:1 ratio respectively, and incubated for 2 hours at 37° C. In the case of the control wells, two wells with Tris buffer were added, without compounds.

After the incubation time, the reagents of the Cortisol kit were added, Cortisol d2 and Cortisol cryptate in sample ratio, Cortisol d2 and cortisol cryptate 2:1:1, in a quantity according to the size of the well as indicated by the supplier (for the negative control of the kit, the cortisol d2 is replaced by the kit's reconstitution buffer). This reaction is incubated for 1 hour at room temperature in order to later read the fluorescence at 665 and 620 nm.

Once the enzyme concentration to be used has been determined, the cortisol kit protocol is continued to determine the efficacy curve for the compounds. As previously done, a plate for HTRF was prepared adding to each well of the reaction buffer, the recombinant 11β-HSD1 enzyme and the compounds to be assayed in a 3:1:1 ratio, respectively. The plate was subsequently incubated at 37° C. for 2 hours.

After the incubation time, the reagents of the cortisol kit, cortisol d2 and cortisol cryptate, are added, and were incubated again for 1 hour at room temperature. Finally, the fluorescence of each well was determined at 665 and 620 nm.
Determination of 11β-HSD1 Oxidase Activity The determination of the 11β-HSD1 oxidase activity is carried out by measuring the concentration of cortisone produced in the reaction with and without the compounds. The Cortisol Kit (Cisbio) product was used for that purpose.

For the analysis, the compounds are reconstituted in DMSO in a stock of 10 mM concentration, from which serial dilutions were prepared for the efficiency curve.

The recombinant 11β-HSD1 enzyme dilutions were prepared in 20 mM Tris Buffer 5 mM EDTA pH 6.0 (Tris buffer).

Initially, the enzyme concentration to be used was determined. For this purpose, a plate for HRTF was prepared with Tris buffer with 100 nM cortisol and 200 µM NADP+, including in the wells of the plate for HTRF together with the enzyme in a 4:1 ratio, respectively, and incubated for 2 hours at 37° C. After this time, the reagents of the Cortisol kit, Cortisol d2 and Cortisol cryptate in sample ratio, Cortisol d2 and cortisol cryptate 2:1:1 were added, incubating this new reaction for 1 hour at room temperature. Subsequently, the fluorescence was determined at 665 and 620 nm.

Once the enzyme concentration to be used has been determined, the Cortisol Kit protocol is continued to determine the efficacy curve of the compounds. An HRTF plate was again prepared, where the reaction buffer, the recombinant 11β-HSD1 enzyme and the compound were added in each well in a 3:1:1 ratio, respectively. The plate was incubated at 37° C. for 2 hours. After the incubation time, the reagents of the cortisol kit, cortisol d2 and cortisol cryptate, were added as indicated above. They were then incubated at room temperature for 1 hour to finally read the fluorescence at 665 and 620 nm.
Determination of 11β-HSD2 Oxidase Activity The concentration of cortisone produced in the reaction, with and without the compounds, was determined using the Cortisol Kit (Cisbio) product in order to evaluate the 11β-HSD2 oxidase activity.

As in the previous assays, the compounds are reconstituted in DMSO to 10 mM stock, in order to subsequently make serial dilutions to determine the efficacy curve.

To determine the IC$_{50}$ of the compounds, a model of donor human hepatic microsomes (BioReclamationIVT Inc.) was used, which was prepared in Tris Buffer 20 mM EDTA 5 mM pH 6.0 (Tris buffer).

To perform the assay, the HTRF plate was prepared containing Tris buffer, 100 nM cortisol and 200 μM NAD⁺. Enzyme is added to the corresponding wells in a 4:1 ratio, respectively, and incubated for 2 hours at 37° C. For the kit control, two wells are added only with Tris buffer.

After the incubation time, the reagents of the Cortisol kit, Cortisol d2 and Cortisol cryptate, in a sample ratio, Cortisol d2 and cortisol cryptate 2:1:1 are added. For the negative control, cortisol d2 was replaced in some wells by the kit's reconstitution buffer. The plate was incubated for 1 hour at room temperature to later read at 665 and 620 nm.

Once the enzyme concentration to be used has been determined, the Cortisol Kit protocol is continued to determine the efficacy curve for the compounds. For this purpose, the reaction buffer was prepared and subsequently, in a plate for HTRF, the reaction buffer, the microsomes in a concentration of 5 mg/mL and the compound in a ratio of 3:1:1, respectively, were added to each well. In the case of reaction controls, the reaction buffer without cortisol and without compound is included for the negative control. For the positive control, no compound is added, and for the kit controls, only the reaction buffer is added to the negative and positive control wells.

After incubating the plate for 2 hours, the reagents of the cortisol kit, cortisol d2 and cortisol cryptate, are added to the corresponding wells as indicated above. They are then incubated at room temperature for 1 hour to finally read the 665 and 620 nm fluorescence.

The results described in Table 1 were obtained from the previously described assays.

TABLE 1

Inhibitory activity of the compounds of formula (I) against the oxidase activity of the enzyme 11β-HSD1 and its selectivity with respect to isoforms 1 and 2 (11β-HSD2).

| Com-pound | 11b-HSD1 reductase (HTRF) IC50 (nM) | 11b-HSD1 oxidase (activ rem %) 100 nM | 11b-HSD1 oxidase (activ rem %) 100 uM | 11b-HSD2 oxidase (activ rem %) Microcosms 100 nM |
|---|---|---|---|---|
| BD44 | 3.9 | 107.0% | 94.3% | 114.1% |
| BD40 | 11.8 | 92.1% | 89.9% | 97.9% |
| BD35 | 9.9 | 91.3% | 104.0% | 79.5% |
| BD45 | 1.1 | 97.4% | 114.0% | 70.2% |
| BD34 | 104 | 109.0% | 77.2% | 68.8% |
| BD46 | 24 | 104.6% | 65.4% | 62.0% |
| BD38 | 102 | 88.1% | 100.5% | 61.9% |
| BD32 | 95.4 | 104.1% | 62.7% | 60.0% |
| BD33 | 9.2 | 107.0% | 75.4% | 59.4% |
| BD42 | 92 | 83.0% | 89.8% | 59.2% |
| BD39 | 97 | 89.4% | 75.3% | 59.2% |
| BD37 | 1.1 | 109.6% | 88.1% | 58.3% |
| BD31 | 147 | 86.1% | 86.20% | 55.4% |
| b-Gly | 138 | 82.5% | 61.30% | 54.1% |
| 665953 | 98 | 98.0% | 102.30% | 54.0% |
| BD41 | 102 | 85.9% | 86.1% | 49.7% |
| BD36 | 102 | 110.3% | 95.3% | 40.1% |

Example 3: Determination of Biopharmaceutical Characteristics of Compounds of Formula (I), BD-40 and BD-44

This application example presents the results of the determination of permeability on BD-40 and BD-44 monolayers, solubility of the compound of formula (I) BD-40 and binding capacity to plasma proteins of the BD-40 compound.

Prior to these analyzes, the analytical methodologies to detect and quantify the BD-40 and BD-44 compounds were standardized. For this purpose, analytical methodologies were developed by tandem uHPLC-MS/MS (Triple Quad 4500, AB Sciex Instruments) for the BD-40 and BD-44 compounds.

The ionization parameters were optimized by direct infusion (1 mL/min) of solutions at 1 μg/mL in a 50:50 acetonitrile (ACN)/water mixture. These parameters for ionization are presented in the following table (Table 2):

TABLE 2

Ionization source parameters for the detection of BD-40 and BD-44 compounds.

| Parameter* | Value |
|---|---|
| TEM | 650.00 |
| GS1 | 50.00 |
| GS2 | 50.00 |
| IS | 3500 |
| CUR | 25.00 |
| CAD | 9.00 |

*GS1: Nebulizer gas. GS2: Drying gas. TEM: Capillary temperature. IS: Ion-spray voltage. CUR: Curtain gas. CAD: Collision gas.

After obtaining the optimal ionization parameters, it was necessary to optimize the fragmentation parameters of each compound; for this purpose, the mass spectrometer was operated in multiple reaction monitoring (MRM), positive mode. To perform the quantification, the transitions 322, 976/135,100 (BD 40), 310,080/135,100 (BD 44), 210,061/193,200 (minoxidil) and 267,072/145,100 (atenolol) were used. The MRM and quantifying fragment parameters for each compound are described in Table 3, where minoxidil and atenolol are also included as markers.

TABLE 3

MRM spectrometric parameters for each BD-40 and BD-44 compounds.

| Parameter | BD-40 | BD-44 | Minoxidil | Atenolol |
|---|---|---|---|---|
| DP | 11.00 | 41.00 | 36.00 | 86.00 |
| CE | 27.00 | 33.00 | 21.00 | 35.00 |
| CXP | 10.00 | 10.00 | 14.00 | 12.00 |

*DP: Declustering potential. CE: Collision energy. CXP: Output energy. The entry potential (EP) was 10.00 in all cases.

After the determination of the mentioned parameters, the chromatographic analysis was carried out. For this purpose, the Ekspert ultraLC 100-XL equipment (AB Sciex Instruments) with autosampler thermostat and column oven was used. A C18 column (Inertsil OSD-4, 3 um, 2.1×100 mm) was used, the injection volume was 10 μL, the flow rate was 0.5 mL/min, and the column temperature was 40° C. The mobile phase was water 10 mM ammonium formate pH 5 at 5% in ACN (A) and ACN 10 mM ammonium formate 5% in water (B). Table 4 presents the elution gradients for each compound.

TABLE 4

Elusion gradients for BD-40 and BD-44 compounds.

| BD-40 | | BD-44 | |
|---|---|---|---|
| Time (min) | % B | Time (min) | % B |
| 0.00 | 5 | 0.00 | 5 |
| 1.00 | 20 | 1.00 | 20 |
| 5.00 | 100 | 3.50 | 60 |
| 7.00 | 100 | 4.00 | 5 |
| 8.00 | 5 | 4.50 | 5 |
| 9.00 | 5 | — | — |

The methods presented were partially validated; for this purpose, specificity, range, linearity, precision and accuracy were evaluated. To carry out this evaluation, standard solutions of each compound (BD-40 and BD-44) were prepared in a concentration range that went from 0.1 to 1000 ppb, in two embodiments. In the first embodiment, a calibration curve was prepared for each compound and the second embodiment comprised standard solutions of the compounds (BD-40 and BD-44) plus the markers minoxidil and atenolol. The solutions were evaluated in triplicate.

These methods were shown to be specific for each compound, and presented linear ranges of at least 3 orders of magnitude, coefficients of determination (R2) of at least 0.984, coefficients of variation for each concentration and each drug of no more than 1.6% with accuracies greater than 93%.

Permeability Analysis on Monolayers of the Compounds of Formula (I), BD-40 and BD-44).

Madin-Darby Canine Kidney (MDCK) cells were used in this assay, which are stably transfected with the gene encoding human P-glycoprotein (hMDR1). These cells were cultured in DMEM medium (Dulbecco's Modified Eagle's Medium) high in glucose and supplemented with 10% fetal bovine serum, 1% 5 mM pyruvate, 1% non-essential amino acids solution X5, 20,000 IU/mL of penicillin G and 20,000 IU/mL of streptomycin, a temperature of 37° C., 90% relative humidity and 5% $CO_2$. These cells were seeded in sterile plates on the fourth day of growth or until reaching 90% confluence.

Ten days before carrying out the transport analysis, cells were seeded in Transwells® inserts (1.12 cm2) at a density of 60,000 cells/cm². The monolayers were supplemented every two days with fresh culture medium. On the day of analysis, the cells were washed 3 times (both compartments) with Hanks Balanced Salt Solution transport buffer, HBSS pH 6.8 at 37° C., then incubated with 500 μL of 10 μM compound solution in the presence of the markers minoxidil (10 μM) and atenolol (10 μM) in the apical compartment and 1.5 mL of buffer in the basolateral compartment (experiment A-B, n=3). In parallel, B-A experiments were performed (1.5 mL of donor solution in basolateral compartment and 0.5 mL buffer in apical). The monolayers were incubated while stirring (50 rpm) at a temperature of 37° C. for a period of 2 hours. Additionally, this assay was performed in the presence of the Pgp inhibitor elacridar (5 μM). After the stir time, the inserts were removed, the compartments were sampled and the cells were transferred to HPLC vials by diluting these samples with mobile phase chromatography. These samples were kept at −20° C. until their analysis time. The mass balance of each compound always remained above 80%.

The bi-directional transport of each compound was parameterized as apparent permeability (Papp) from the transcellular flux values from Fick's first law, according to equation (1), $$Papp=(dM\_R)/(A \cdot dT \cdot C\_D) \quad (1)$$

Where dMR corresponds to the amount of compound in the receptor compartment at time t (nmol): A is the area of the monolayer (cm²); dT is the duration of the experiment (s); and CD is the donor concentration at time zero (μM). For each compound, the efflux ratio (ER) was obtained according to equation (2), $$ER = [Papp]_{(B-A)} / [Papp]_{(A-B)} \quad (2)$$

In this equation, PappB-A is the apparent permeability of the compound in the direction of secretion and PappA-B is the apparent permeability of the compound in the direction of absorption. An ER>2 in the absence of elacridar, and similar to 1 in the presence of elacridar, confirms active pgP-mediated secretion. Table 5 shows the PappA-B and ER values for BD-40 and BD-44.

TABLE 5

Apparent permeability and flow rate of the compounds of formula (I) BD-40 and BD-44.

| BD-40 | | | BD-44 | | |
|---|---|---|---|---|---|
| $Papp^{A-B}$ | SEM | ER | $Papp^{A-B}$ | SEM | ER |
| 1.36E−06 | 5.33E−07 | 0.50 | 4.98E−05 | 2.65E−06 | 0.94 |

Papp BD-40 and BD-44 values were higher than those of the high permeability marker minoxidil (p<0.01). The Papp of the integrity marker atenolol was less than 0.5×10−6 cm/s. The ER values were not higher than 2 and were not affected by the presence of the inhibitor pgP elacridar, so it is ruled out that BD-40 and BD-44 are P-glycoprotein substrates.

Solubility of the BD-40 Compound of Formula (I).

To study the solubility of BD-40 in the pH range of the gastrointestinal tract, flasks with regulatory buffers at pH 1.2; 4.5; and 6.8 were used. A stock solution of 100 mM was prepared in DMSO that was added in volumes established on the buffers until the appearance of turbidity was observed. These solutions were prepared in triplicate in final DMSO concentrations of 0.5 to 5.0% V/V of each buffer, then were incubated at 37° C. with vigorous stirring for 48 hours, then another 48 hours but without stirring. The samples were centrifuged and the supernatant was diluted with mobile phase chromatography to be later analyzed by μHPLC-Ms/Ms. The solubility value at each pH was obtained from the intercept of the straight line solubility versus % DMSO. Table 6 presents the aqueous solubility values of BD-40 in the pH range 1.2-6.8.

TABLE 6

Aqueous solubility of BD-40 in the gastrointestinal pH range

| pH | Solubility (μg/mL) | SEM |
|---|---|---|
| 1.7 | 96.16 | 15.47 |
| 4.5 | 64.12 | 10.43 |
| 6.8 | 59.23 | 7.82 |

Analysis of the Plasma Protein Binding Capacity of the BD-40 Compound of Formula (I).

To carry out this study, the commercial Transil XL PPB Binding Kit, v2, Sovicell was used, following the manufacturer's recommendations.

According to the results, the plasma protein binding of BD-40 was 98.3±1.9%

Determination of the plasma protein binding of the drug allows the efficacy of the drug to be defined. When bound to plasma protein, the drug can cross cell membranes reaching its therapeutic target. In addition, less drug is lost by excretion, allowing the effective therapeutic dose of the compound to be at its target of action. In this case, the BD-40 compound of formula (I) exhibits high efficacy percentages, with a lower loss of the drug.

Example 4: In Vivo Assay with BD-40 and BD-44 Compounds of Formula (I)

For the evaluation of the BD-40 and BD-44 compounds in vivo, male C57BL/6J mice, approximately 9-12 weeks old, were used, which were provided by the Science & Life Foundation animal facility.

The animals were classified according to weight and divided into the following groups (Table 7):

TABLE 7

Classification of individuals for in vivo assays of the compounds of formula (I) BD-40 and BD-44.

| Compound | Group | Number of animals | Administration routes | Dose (mg/Kg) | Conc. dose (mg/mL) | Dose volume (mL/Kg) |
|---|---|---|---|---|---|---|
| BD-40 | 1 | 30 | I.V. | 2 | 0.4 | 5 |
|  | 2 | 71 | V.O. | 10 | 1 | 10 |
| BD-44 | 3 | 30 | I.V. | 2 | 0.4 | 5 |
|  | 4 | 71 | V.O. | 10 | 1 | 10 |

I.V.: intravenous administration,
V.O: oral administration.

The solution containing the dose of BD-40 and BD-44 was formulated in a vehicle containing 30% dimethyl sulfoxide (DMSO). 20% Kolliphor and 50% PBS at a concentration of 1 mg/mL. From this solution, a 0.4 mg/mL dilution was made for IV administration.

In intravenous (IV) administration, after each compound was administered to the mice, the mice were separated into groups of 3 and were euthanized at times 5, 10, 15, 30, 60, 120, 240, 260, 480 and 1440 minutes. For oral administration (V.O), the mice were separated into groups of 3 and were euthanized at times 15, 30, 60, 120, 240, 260, 480 and 1440 minutes. To obtain zero-time assays, mice were used to which no compound was administered.

Whole blood was obtained from each animal (in microtubes with EDTA); these samples were centrifuged at 9000 g at a temperature of 4° C. for a period of 5 minutes, obtaining the plasma which was stored at −80° C.

In addition, organs such as brain, liver, muscle, epididymal fat, heart and kidney were obtained from the animals, which were frozen in liquid nitrogen and stored at −80° C.

Plasma samples and brain, liver, epididymal fat, and muscle (tissue) samples were analyzed. 2× in volume of water (weight/volume) was added to the tissue samples while 4× in volume of water (weight/volume) was added to the muscle mixture, after which they were homogenized using a Bullet Blender equipment (Next Advance, USA).

All samples were analyzed as a single point by LC-MS/MS in accordance with the analytical methodology already standardized and presented in application example 3.

To begin, a calibration curve was run. For this purpose, the controls, the plasma and organ samples were prepared by adding 180 μL of cold acetonitrile to these, then vortexed for 15 seconds and centrifuged at 6100 g for 30 seconds at 4° C. The supernatant which was obtained from this procedure was diluted in 2 volumes of 0.2% formic acid in water and transferred to a vial that will allow it to be injected into LC-MS/MS.

The conditions for the LC-MS/MS analysis were:
HPLC: Eksigent UltraLC 100
Autosampler: Eksigent UltraLC 100-XL at RT
Mobile phase: A-0.1% formic acid in water; B-0.1% formic acid in acetonitrile.
Column: YMC Triart 1.9 μm; 2.0×50 mm
Injection volume: 2 μL
Gradient: 5% B for 0.25 min→5-95% B for 0.75 min→95% B for 2 min→95-5% B for 0.25 min→5% B for 0.25 min
Flow: 0.6 mL/min
Mass Spectrometer: Applied Biosystems/SCIEX QTRAP 4500
Interface: TurbolonSpray (ESI) at 600° C.
Software: Analyst.

An analysis was performed for both compounds in the positive mode, detecting the parental ion 323.4 [M 1] and the product ion 135.2 [M+1] for BD-40; and the parent ion 310.4 [M+1] and the product ion 135.2 [M+1] for BD-44.

a) Results of the BD-40 Pharmacokinetic Analysis
Analysis of the BD-40 Compound Plasma Samples The results obtained for the pharmacokinetic parameters of BD-40 in plasma are summarized in Table 8. The mean time (hr) of the drug was 3.30 when it was administered intravenously and 0.864 hrs when it was administered orally.

TABLE 8

Pharmacokinetic analysis results for BD-40 in plasma

| Route | Dose (mg/Kg) | $C_0$/Cmax (ng/mL) | tmax (hr) | $AUC_{final}$ (hr · ng/mL) | $AUC_{Inf}$ (hr · ng/mL) | $AUC_{Extr}$ (%) | Vz (L/kg) | CL (L/hr/kg) | MRTInf (hr) | $t_{1/2}$ (hr) | F (%) |
|---|---|---|---|---|---|---|---|---|---|---|---|
| IV | 2 | 2200 | NC | 649 | 623 | 5.240 | 15.30 | 3.21 | 1.46 | 3.30 | — |
| PO | 3 | 393 | 0.5 | 575 | 596 | 3.6 | 168 | 16.8 | — | 0.538 | 19.1 |

Figure 1:
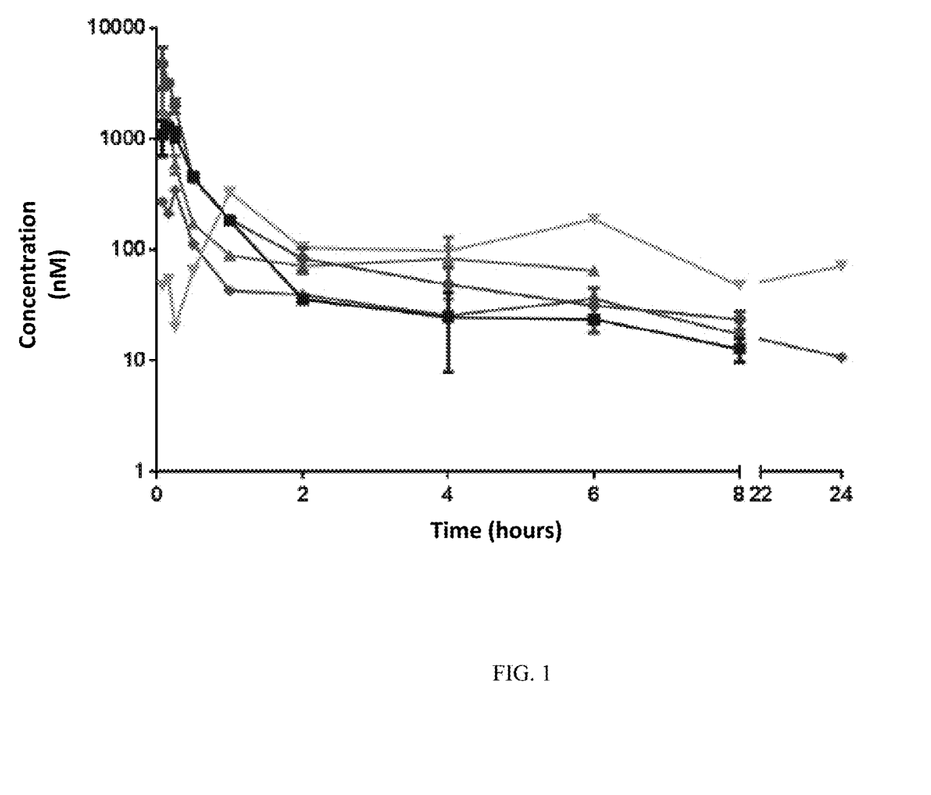
FIG. 1.—BD40 (nM) levels detected in plasma and other tissues at different time periods, IV dose (2 mg/Kg). BD-40 concentration detected by means of single point analysis by LC-MS/MS in different tissues: corresponds to analysis in plasma, corresponds to analysis in brain tissue, corresponds to analysis in liver, corresponds to analysis in epididymis fat and corresponds to analysis in muscle.
Figure 2:
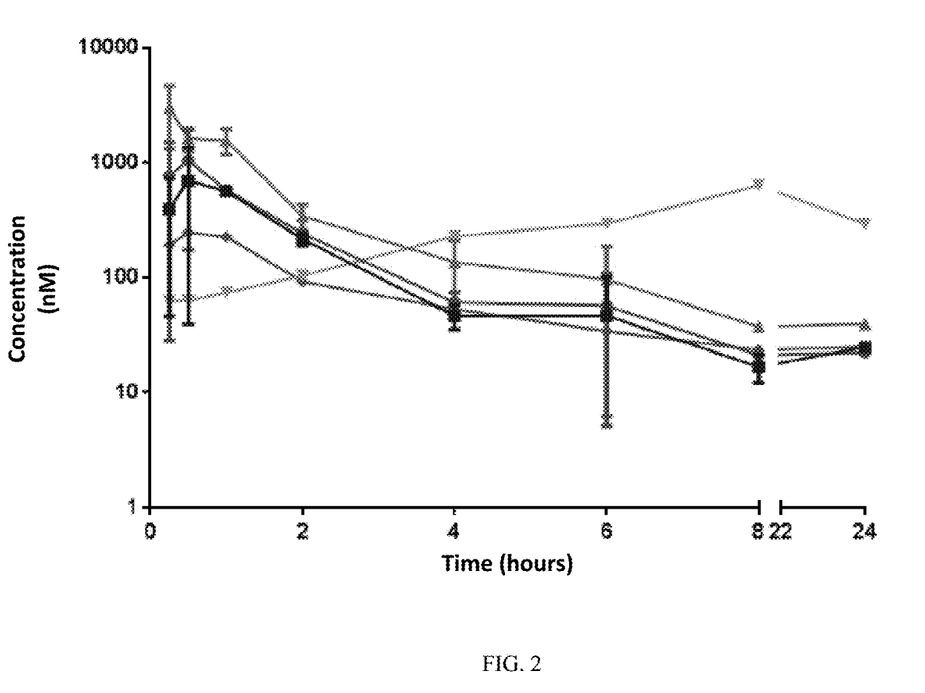
FIG. 2.—BD40 (nM) levels detected in plasma and other tissues at different time periods, oral dose (10 mg/Kg). BD-40 concentration detected by means of single point analysis by LC-MS/MS in different tissues: corresponds to analysis in plasma corresponds to analysis in brain tissue, corresponds to analysis in liver, corresponds to analysis in epididymis fat and corresponds to analysis in muscle.

IV: intravenous administration,
PO: oral administration,
NC: Not determined or calculated The detection and analysis of pharmacokinetic parameters for the BD-40 compound was also carried out in brain, liver, fat tissue and muscle. It is observed that the BD-40 compound has good bioavailability and can be detected in the different tissues of the organs evaluated (brain, liver, fat and muscle), both when it was administered orally and intravenously (FIGS. 1 and 2).

b) Results of the BD-44 Pharmacokinetic Analysis

Figure 3:
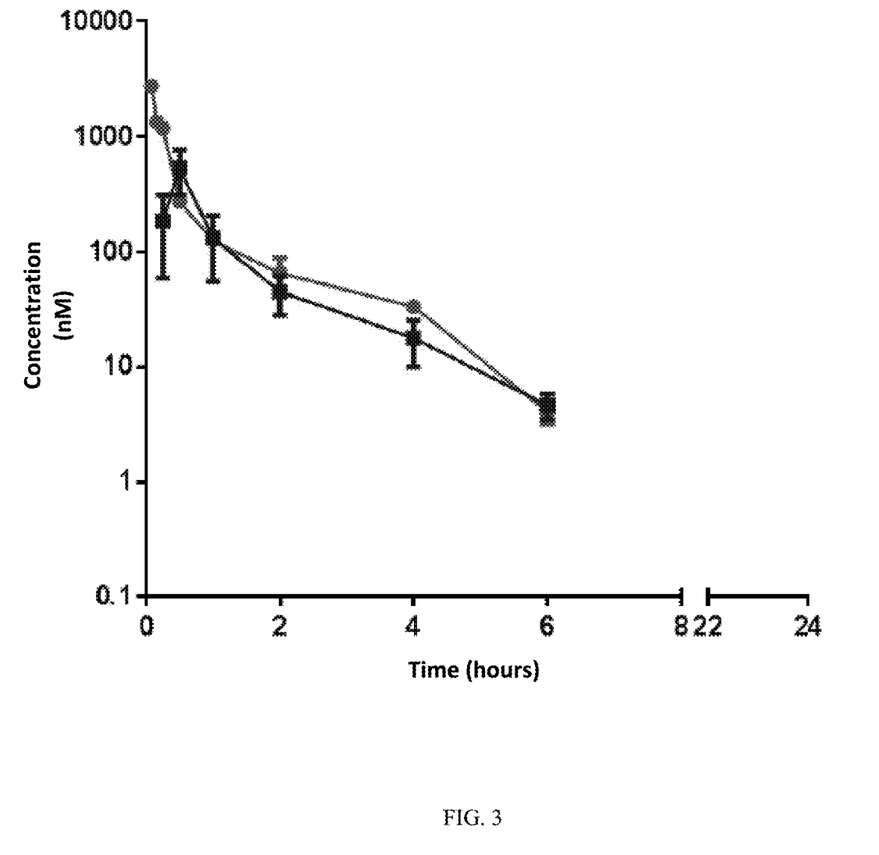
FIG. 3.—Graph summarizing levels of BD-44 compound detected in plasma at different times, IV dose (2 mg/Kg) and oral dose (10 mg/Kg). corresponds to IV dose detection and corresponds to oral dose detection.

The results obtained for the pharmacokinetic parameters of BD-44 are summarized in Table 9. The mean time (hrs) of elimination of the drug was 1.02 when it was administered intravenously and 1.05 when it was administered orally. The BD-44 compound was detected up to 6 hours post administration, both when it was administered intravenously and orally (FIG. 3).

Although a low apparent availability of BD-44 was observed in plasma and was not detected in the tissues assayed, this corresponds to an initial analysis without taking the drug administration regimen into account.

TABLE 10

Pharmacokinetic analysis results for BD-44 in plasma

| Route | Dose (mg/Kg) | $C_0$/Cmax (ng/L) | tmax (hr) | $AUC_{final}$ (hr · ng/mL) | $AUC_{Inf}$ (hr · ng/mL) | $AUC_{Extr}$ (%) | Vz (L/kg) | CL (L/hr/kg) | $t_{1/2}$ (hr) | Rsq | F (%) |
|---|---|---|---|---|---|---|---|---|---|---|---|
| IV | 2 | 1800 | NC | 368 | 369 | 0.672 | 7.95 | 5.42 | 1.02 | 0.954 | — |
| PO | 10 | 173 | 0.5 | 146 | 148 | 1.39 | 102 | 67.3 | 1.05 | 0.985 | 8.00 |

IV: intravenous administration.

PO: oral administration.

NC: Not determined or calculate

REFERENCES

Kadmiel M. and Cidlowski J A. (2013.) Glucocorticoid receptor signaling in health and disease. Trends Pharmacol Sci.; 34(9):518-30).

Masuzaki H, Yamamoto H, Kenyon C J, Elmquist J K, Morton N M, Paterson J M. (2003). Transgenic amplification of glucocorticoid action in adipose tissue causes high blood pressure in mice. J Clin Invest 2003; 112: 83-90).

Livingstone D E W, Jones G C, Smith K, Jamieson P M, Andrew R, Kenyon C J, Walker B R. (2000). Understanding the role of glucocorticoids in obesity: tissue-specific alterations of corticosterone metabolism in obese zucker rats. Endocrinology 2000; 141: 560-3.

Tomlinson J W, Walker E A, Bujalska I J, Draper N, Lavery G G, Cooper M S. (2004). 11β-Hydroxysteroid dehydrogenase type 1: A tissue-specific regulator of glucocorticoid response. Endocrine Reviews; 25: 831-66).

Wake D. J. y Walker B. R. (2004). 11-beta-hydroxysteroid dehydrogenase type 1 in obesity and the metabolic syndrome. Mol Cell Endrocrinol 215(1-2):45-54.

Walker D. J. y Walker B. R (2006). Cortisol-cause and cure for metabolic syndrome?. Diabet Med 23(12): 1281-1288.

The invention claimed is:

1. A compound of formula (I), wherein L1 is CH or nitrogen, provided that if L1 is nitrogen then L1 is different from L3; L2 is carbon or nitrogen, provided that if L2 is nitrogen then R1 is not present; L3 is carbon or nitrogen, provided that if L3 is nitrogen then R2 is not present; R1, R2 and R3 are independently selected from a hydrogen atom, F, Br, Cl, $NO_2$, a linear or branched $C_{1-4}$ alkyl group, or an OR group, where R is H or a linear or branched $C_{1-4}$ alkyl group, or a pharmaceutically acceptable salt, solvate or hydrate thereof.

2. The compound of claim 1, wherein the compound is selected from 1-phenyl-2-(3-adamantyl-1,2,4-oxadiazol-5-yl)ethane (BD-31), 1-(4-methoxyphenyl)-2-(3-adamantyl-1,2,4-oxadiazol-5-yl)ethane (BD-32), 1-(4-chlorophenyl)-2-(3-adamantyl-1,2,4-oxadiazol-5-yl)ethane (BD-33), 1-(4-fluorophenyl)-2-(3-adamantyl-1,2,4-oxadiazol-5-yl)ethane (BD-34), 1-(4-bromophenyl)-2-(3-adamantyl-1,2,4-oxadiazol-5-yl)ethane (BD-35), 1-(4-methylphenyl)-2-(3-adamantyl-1,2,4-oxadiazol-5-yl)ethane (BD-36), 1-(4-hydroxyphenyl)-2-(3-adamantyl-1,2,4-oxadiazol-5-yl)ethane (BD-37), 1-(3-methoxyphenyl)-2-(3-adamantyl-1,2,4-oxadiazol-5-yl)ethane (BD-38), 1(4-pyridyl)-2-(3-adamantyl-1,2,4-oxadiazol-5-yl)ethane (BD-39), 1-(3-methylphenyl)-2-(3-adamantyl-1,2,4-oxadiazol-5-yl)ethane (BD-40), 1-(4-tert-butylphenyl)-2-(3-adamantyl-1,2,4-oxadiazol-5-yl)ethane (BD-41), 1-(3-fluorophenyl)-2-(3-adamantyl-1,2,4-oxadiazol-5-yl)ethane (BD-42), 1-(3-pyridyl)-2-(3-adamantyl-1,2,4-oxadiazole-5-yl)ethane (BD-44), 1-(2-pyridyl)-2-(3-adamantyl-1,2,4-oxadiazol-5-yl)ethane (BD,45), 1-(4-nitrophenyl)-2-(3-adamantyl-1,2,4-oxadiazol-5-yl)ethane (BD-46), or a pharmaceutically acceptable salt, solvate or hydrate thereof.

3. A pharmaceutical composition, comprising a therapeutically effective amount of the compound of claim 1 or a pharmaceutically acceptable salt, solvate or hydrate thereof in a pharmaceutically acceptable solvent.

4. A method of inhibiting 11-beta dehydrogenase type 1 enzyme, comprising administering a therapeutically effective amount of the compound of claim 1 or a pharmaceutically acceptable salt, solvate or hydrate thereof to a patient in need thereof.

5. A process for the preparation of a compound of claim 1, wherein the process comprises the following steps:
a) preparing a mixture of hydroxylamine hydrochloride and sodium carbonate in ethanol and glycerol, stirring overnight at room temperature,
b) reacting the mixture from a) with a solution of 1-cyanoadamantane and aluminum chloride in ethanol to form a suspension,
c) stirring the resulting suspension under reflux conditions for 10 hours,
d) after 10 hours, removing residual ethanol by vacuum filtration, partitioning the residue with water and dichloromethane, and extracting the aqueous phase with dichloromethane,
e) washing the resulting organic phase with brine and drying with anhydrous sodium sulfate, obtaining a white product corresponding to the parent 1-adamantylamidoxime (1)

(1)

f) reacting the parent compound (1) with 2-chloro-4,6-dimethoxy-1,3,5-triazine in N-methylmorpholine or 1,4-dioxane, in the presence of a substituted propionic acid, and
g) purifying the product obtained from the reaction in f).

6. The process of claim 5, wherein in step f) the substituted propionic acid is selected from 3-phenyl propionic acid, 3-(4-methoxyphenyl) propionic acid, 3-(4-chlorophenyl) propionic acid, 3-(4-fluorophenyl) propionic acid, 3-(4-bromophenyl) propionic acid, 3-(p-tolyl) propionic acid, 3-(4-hydroxyphenyl) propionic acid, 3-(3-methoxyphenyl) propionic acid, 3-(3-methylphenyl) propionic acid, 3-(4-tert-butylphenyl) propionic acid, 3-(3-fluorophenyl) propionic acid, 3-(2-pyridyl) propionic acid, 3-(3-pyridyl) propionic acid, 3-(4-pyridyl) propionic acid, and 3-(4-nitrophenyl) propionic acid.

* * * * *